(12) United States Patent
Cho et al.

(10) Patent No.: US 11,014,694 B2
(45) Date of Patent: May 25, 2021

(54) TESTING APPARATUS HAVING VACUUM CHAMBER, CAPABLE OF GROUND TESTING, AND TESTING METHOD USING SAME

(71) Applicant: KOREA INSTITUTE OF CIVIL ENGINEERING AND BUILDING TECHNOLOGY, Goyang-si (KR)

(72) Inventors: Changbeck Cho, Paju-si (KR); Hyusoung Shin, Goyang-si (KR); Yongho Yoo, Incheon (KR); Jangguen Lee, Goyang-si (KR); Hosang Ahn, Goyang-si (KR); Taeil Chung, Daejeon (KR)

(73) Assignee: KOREA INSTITUTE OF CIVIL ENGINEERING AND BUILDING TECHNOLOGY, Goyang-si (KR)

( * ) Notice: Subject to any disclaimer, the term of this patent is extended or adjusted under 35 U.S.C. 154(b) by 121 days.

(21) Appl. No.: 16/605,428

(22) PCT Filed: Jul. 17, 2018

(86) PCT No.: PCT/KR2018/008070
§ 371 (c)(1),
(2) Date: Oct. 15, 2019

(87) PCT Pub. No.: WO2019/022428
PCT Pub. Date: Jan. 31, 2019

(65) Prior Publication Data
US 2021/0122503 A1 Apr. 29, 2021

(30) Foreign Application Priority Data
Jul. 24, 2017 (KR) .......................... 10-2017-0093478

(51) Int. Cl.
*G01N 3/60* (2006.01)
*G01N 3/02* (2006.01)
(Continued)

(52) U.S. Cl.
CPC ................ *B64G 7/00* (2013.01); *G01N 3/02* (2013.01); *G01N 3/60* (2013.01); *G01N 33/24* (2013.01);
(Continued)

(58) Field of Classification Search
CPC  G01N 3/02; G01N 3/60; G01N 33/24; G01N 2203/0234; B64G 2007/005; B64G 7/00; G01M 99/002
See application file for complete search history.

(56) References Cited

U.S. PATENT DOCUMENTS 9,034,143 B2    5/2015  Cho et al.
2010/0040441 A1*  2/2010  Obikane ........... H01L 21/67772
                                                       414/222.01
2011/0107858 A1*  5/2011  Obikane ............ G01R 31/2893
                                                           73/866.5

FOREIGN PATENT DOCUMENTS

JP      2010-091132 A    4/2010
KR      10-1142609 B1    5/2012
(Continued)

OTHER PUBLICATIONS

International Search Report for PCT/KR2018/008070 dated Oct. 29, 2018 from Korean Intellectual Property Office.

*Primary Examiner* — Brandi N Hopkins
(74) *Attorney, Agent, or Firm* — Paratus Law Group, PLLC (57) ABSTRACT

Disclosed is a testing apparatus and a testing method using the same, the apparatus having soil in a vacuum chamber includes: a buffer chamber having an entrance/exit opening through which an object to be inspected is inserted, and a (Continued)

first door for opening and closing the entrance/exit opening; a testing chamber divided at one side of the buffer chamber so as to be separated therefrom, and having a connection passage communicating with the buffer chamber; a shutter unit for opening and closing the connection passage; a soil storage part disposed inside the testing chamber, and accommodating soil for testing the object to be inspected; and a vacuum generation means for suctioning air inside the buffer chamber and the testing chamber so as to create a vacuum state.

15 Claims, 8 Drawing Sheets

(51) Int. Cl.
     *B64G 7/00*          (2006.01)
     *G01N 33/24*      (2006.01)

(52) U.S. Cl.
     CPC .................. *B64G 2007/005* (2013.01); *G01N 2203/0234* (2013.01)

(56) References Cited

FOREIGN PATENT DOCUMENTS

| | | |
|---|---|---|
| KR | 10-2012-0089984 A | 8/2012 |
| KR | 10-1583604 B1 | 1/2016 |

\* cited by examiner

TESTING APPARATUS HAVING VACUUM CHAMBER, CAPABLE OF GROUND TESTING, AND TESTING METHOD USING SAME

CROSS-REFERENCE TO PRIOR APPLICATIONS

This application is a National Stage Patent Application of PCT International Patent Application No. PCT/KR2018/008070 (filed on Jul. 17, 2018) under 35 U.S.C. § 371, which claims priority to Korean Patent Application No. 10-2017-0093478 (filed on Jul. 24, 2017), which are all hereby incorporated by reference in their entirety.

BACKGROUND

The present invention relates to a testing apparatus, and more specifically, to a testing apparatus including a vacuum chamber having a thermal condition and a vacuum condition similar to that of a space environment and provided with soil (ground) therein so as to perform a ground test of construction equipment and the like in the space environment, and a testing method using the same.

Thermal vacuum chambers, which test appropriateness of various components of a satellite in a space environment or an extreme environment, should be fundamentally maintained in a vacuum state and require a temperature adjustment performance which increases or decreases a temperature for a predetermined time so as to make a high or extremely low temperature environment.

Therefore, the thermal vacuum chamber is made of a metal material that withstands high pressures, high temperatures, extremely low temperatures, an inside thereof is sealed to make a high vacuum environment and is maintained in an extremely low temperature environment by introducing an extremely low temperature refrigerant, such as liquid nitrogen (LN2), thereinto, and the thermal vacuum chamber is formed to change a temperature therein to a high temperature by operating a heater mounted therein.

Conventional thermal vacuum chambers, which simulate a space environment, mainly simulate only a heated and vacuum environment, but soil (ground) should be provided in a chamber having a simulated heated and vacuum environment so that equipment, such as construction equipment, which is important to an interaction with ground, is tested in a space environment.

However, a case in which the conventional thermal vacuum chambers have soil is unusual. Even when a conventional thermal vacuum chamber has soil, the quantity of the soil is small so that a structure and operation of the thermal vacuum chamber are not substantially different from those of the conventional thermal vacuum chambers, and thus reliability of the ground test cannot be ensured.

However, when a great deal of ground is included in a thermal vacuum chamber, a large quantity of out-gas comes out of the ground in a process of reaching a vacuum state so that it is difficult to reach and maintain a vacuum state, but this has not been considered.

Since water, air, and the like are included in soil, when the soil is included in the thermal vacuum chamber, the soil is baked at a high temperature, and the water and air included in the soil are removed and put in the chamber. Even when the pre-conditioned soil is put in the chamber, out-gas, which is not separated from the soil, is generated in the process of reaching a vacuum state, and reaching a target vacuum state takes a long time due to the out-gas. Therefore, a problem occurs that preparing a test takes a long time and, when the quantity of soil increases, a pre-test preparation period increases in proportion to the quantity of soil.

Further, when the chamber including ground is opened due to replacement of a test specimen in the vacuum chamber or replacement of measurement equipment, the ground is in contact with air, and thus a problem occurs that the above-described pre-conditioning operation should be re-performed. When the pre-conditioning operation that requires a long time should be re-performed whenever the chamber including ground is opened, a problem of a long test time occurs, and thus efficiency is considerably decreased.

Further, when the test specimen is put in the testing chamber including soil and the testing chamber is vacuum-exhausted, various types of out-gas that comes out of the soil are attached to the test specimen, and thus the test specimen is contaminated. In this case, objectives of the test cannot be achieved, and the reliability for the performed test can be considerably decreased.

SUMMARY

The present invention is directed to providing a testing apparatus having a thermal condition and/or a vacuum condition similar to that of a space environment and provided with soil (ground) therein so as to efficiently perform a ground test of construction equipment, test specimens, or the like in the space environment, and a testing method using the same.

Particularly, the present invention is directed to providing a testing apparatus and a testing method using the same, wherein, when the vacuum chamber is opened for replacement of a test specimen or equipment after a test is completed in a ground vacuum chamber, the testing apparatus prevents external air from being introduced into the ground vacuum chamber and suppresses out-gas from being generated from the soil (the ground) so as to reduce a test time and increase efficiency.

One aspect of the present invention provides a testing apparatus including a vacuum chamber for a ground test which includes a buffer chamber that includes an entrance through which an object to be inspected is inserted and a first door that opens or closes the entrance, a testing chamber that is separated from one side of the buffer chamber and includes a connection passage communicating with the buffer chamber, a shutter unit configured to open or close the connection passage, a soil storage part which is disposed in the testing chamber and in which soil is accommodated for testing the object to be inspected on the ground, and a vacuum generation unit configured to suction air in the buffer chamber and the testing chamber so as to make the buffer chamber and the testing chamber be in a vacuum state.

Another aspect of the present invention provides a method of testing an object to be inspected under a vacuum state using the testing apparatus according to the present invention which includes (S1) inserting a soil storage part in which soil is accommodated into a testing chamber, (S2) opening a first door of a buffer chamber, inserting an object to be inspected into the buffer chamber through an entrance, and closing the first door, (S3) making insides of the buffer chamber and the testing chamber be in a vacuum state using a vacuum generation unit, (S4) operating a shutter unit in a forward direction to open a connection passage and transferring the object to be inspected from the buffer chamber to the testing chamber, (S5) operating the shutter unit in a reverse direction to close the connection passage, (S6) performing a predetermined test on the object to be inspected on the soil in the testing chamber, (S7) operating the shutter unit in the forward direction to open the connection passage and transferring the object to be inspected from the testing chamber to the buffer chamber, (S8) operating the shutter unit in the reverse direction to close the connection passage, and (S9) opening the first door of the buffer chamber so that the object to be inspected is extracted from the inside of the buffer chamber to an outside thereof through the entrance.

According to the present invention, an object to be inspected is inserted into a buffer chamber separated from a testing chamber, and the tested object to be inspected is transferred from the testing chamber to the buffer chamber so as to be extracted from the buffer chamber, and thus a vacuum state of the testing chamber can be maintained in a process of inserting and extracting the object to be inspected or a process of replacing measurement equipment.

Therefore, it is not necessary to reperform pre-conditioning on soil accommodated in the soil storage part in the testing chamber, and thus a test time can be reduced, and test efficiency can be remarkably increased.

DETAILED DESCRIPTION

Hereinafter, a testing apparatus and a testing method according to the present invention will be described in detail with reference to the accompanying drawings.

Figure 1:
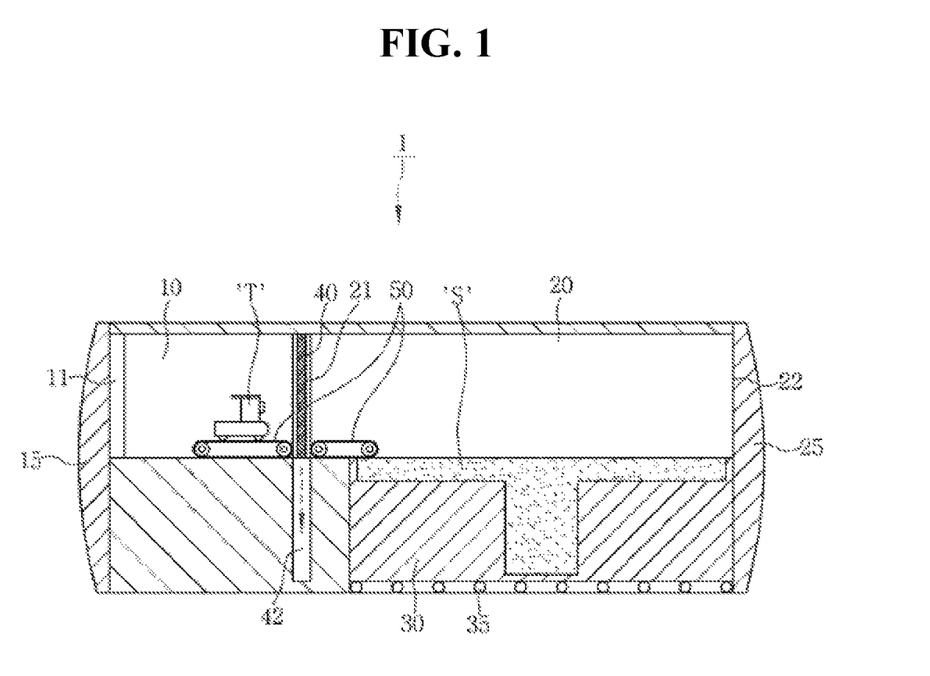
FIG. 1 is a cross-sectional view of a testing apparatus according to one embodiment of the present invention.
Figure 2:
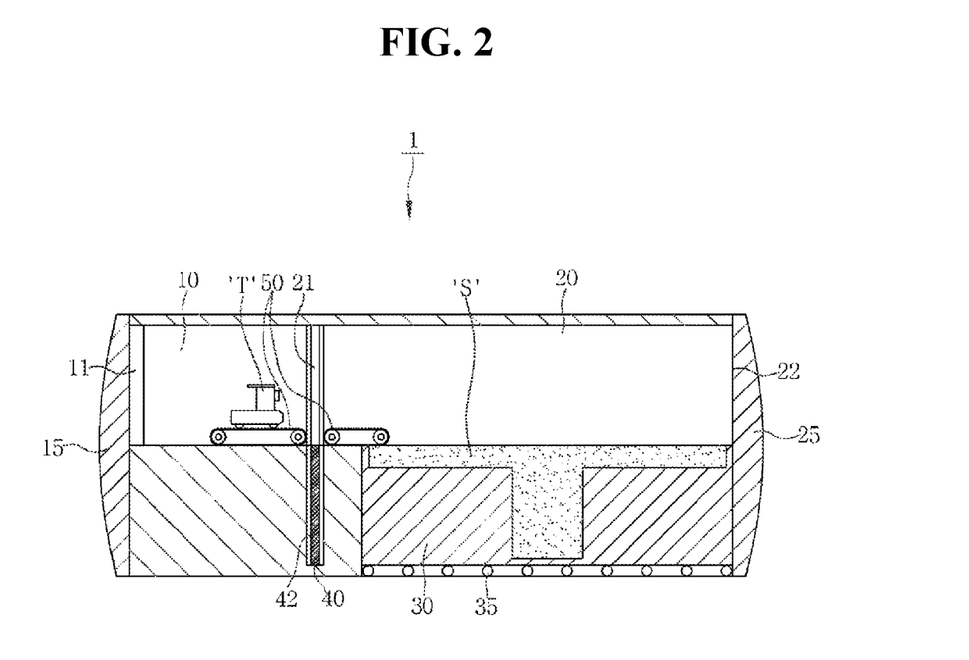
FIG. 2 is a cross-sectional view illustrating an operational example of the testing apparatus shown in FIG. 1.
Figure 3:
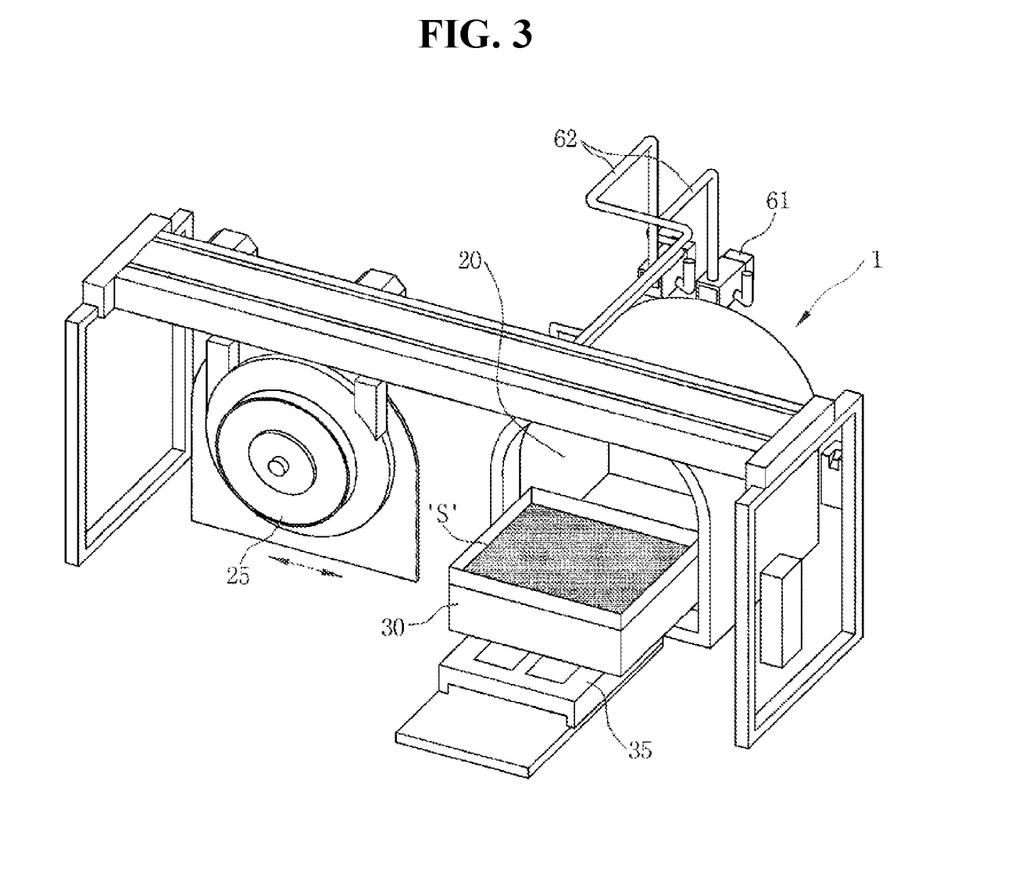
FIG. 3 is a perspective view illustrating a part of the testing apparatus shown in FIG. 1.

Referring to FIGS. 1 to 3, a testing apparatus 1 according to one embodiment of the present invention includes a buffer chamber 10 into which an object T to be inspected is inserted, a testing chamber 20 that performs a ground test of the object to be inspected, a shutter unit that is opened or closed between the buffer chamber 10 and the testing chamber 20, a soil storage part 30 which is mounted in the testing chamber 20 and in which soil S for the ground test of the object T to be inspected is stored, and a vacuum generation unit that makes insides of the buffer chamber 10 and the testing chamber 20 be in a vacuum state.

The buffer chamber 10 is separated from one side of the testing apparatus 1, and an entrance 11 into which the object T to be inspected is inserted is formed on one surface of the buffer chamber 10 and is open. Further, the entrance 11 is provided with a first door 15 that opens or closes the entrance 11. The first door 15 may be formed to be the same as or similar to a door formed in a known thermal vacuum chamber and may be pressed against the entrance 11 while maintaining a sealed state so as to close the entrance 11.

The other side of the buffer chamber 10 is formed to be open to communicate with a connection passage 21 formed on one side of the testing chamber 20. Transfer units are mounted on both sides of the connection passage 21 between the buffer chamber 10 and the testing chamber 20 and move between the buffer chamber 10 and the testing chamber 20 to transfer the object T to be inspected to the buffer chamber 10 or the testing chamber 20. As the transfer unit, an industrial multi joint manipulator or the like may be used, but a transfer conveyor 50 that is bidirectionally moved by a motor (not shown) may be used in the embodiment.

In the buffer chamber 10, when the object T to be inspected is on standby before being inserted into the testing chamber 20 or when the ground test of the object T to be inspected is not required, a predetermined test may be performed on the object to be inspected.

The testing chamber 20 is separated from one side of the buffer chamber 10 and includes the connection passage 21 that is open to communicate with one side of the buffer chamber 10. The testing chamber 20 performs a ground test for the object T to be inspected.

An opening 22 communicating with the outside is formed at the other side of the testing chamber 20, and a second door 25 that opens or closes the opening 22 is mounted on one side of the opening 22. Similar to the first door 15, the second door 25 may be formed to be the same as or similar to the door formed in the known thermal vacuum chamber and may be pressed against the opening 22 while maintaining a sealed state so that the opening 22 is closed. The second door 25 may be formed to move inward or outward of the testing chamber 20 along a door movement frame provided outside the testing chamber 20.

Although not shown in the drawings, a test robot may be provided in the testing chamber 20, wherein the test robot transfers the object T to be inspected to a test position of the soil storage part 30 on the transfer conveyor 50 so that a predetermined test is performed and transfers the object T to be inspected to the transfer conveyor 50 after the test.

A heating device and/or a cooling device may be provided in the buffer chamber 10 and the testing chamber 20 to perform a heat performance test on the object T to be inspected, and the heating device and the cooling device may use a heating device and a cooling device formed in a known thermal vacuum chamber.

The shutter unit opens or closes the connection passage 21 so that the buffer chamber 10 and the testing chamber 20 are separated from or communicate with each other. In the embodiment, the shutter unit may include a shutter plate 40 that opens or closes the connection passage 21 by vertically sliding in the connection passage 21 and a shutter operating part (not shown) that vertically moves the shutter plate 40.

The shutter plate 40 opens or closes the connection passage 21 by sliding inward or outward of a shutter accommodation groove 42 formed below the connection passage 21. A sealing material (not shown), such as rubber or silicone, for maintaining sealing is mounted on an edge portion of the shutter plate 40.

The shutter operating part may include a linear motion system, which includes a power transmission device including a pneumatic cylinder, a motor, a ball screw or a chain, and the like, or a known linear motion system such as a linear motor system.

The soil storage part 30 is disposed in the testing chamber 20 and stores soil S for the ground test of the object T to be inspected. The soil storage part 30 is formed in a box form having an open upper surface and is formed to come out of the testing chamber 20 through the opening 22 of the testing chamber 20.

A slide rail 35 that guides movement of the soil storage part 30 may be mounted below the testing chamber 20 so that the soil storage part 30 may be easily inserted into or extracted from the testing chamber 20 through the opening 22.

Figure 4:
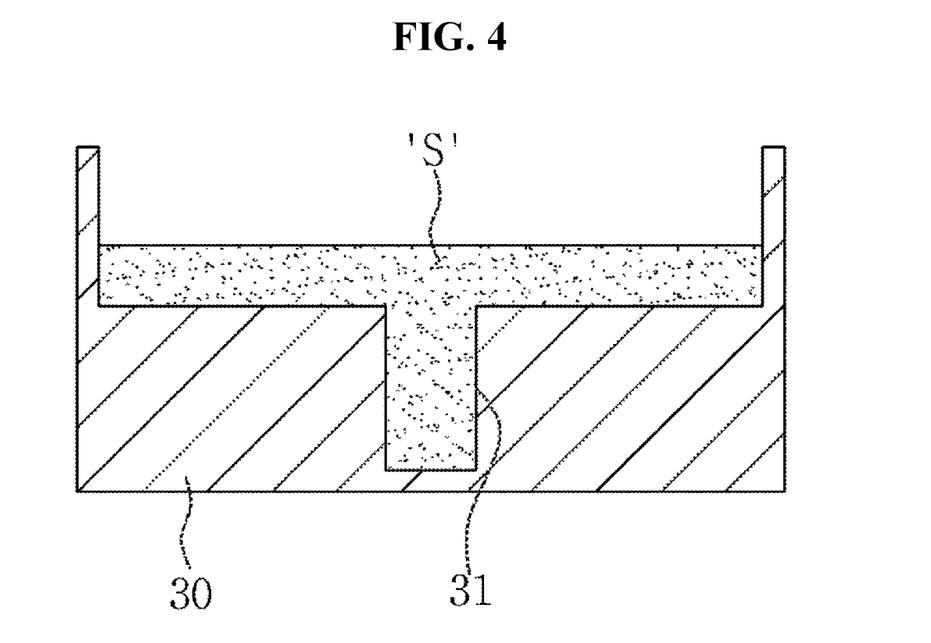
FIG. 4 is a cross-sectional view illustrating a soil storage part of the testing apparatus according to one embodiment of the present invention.
Figure 5:
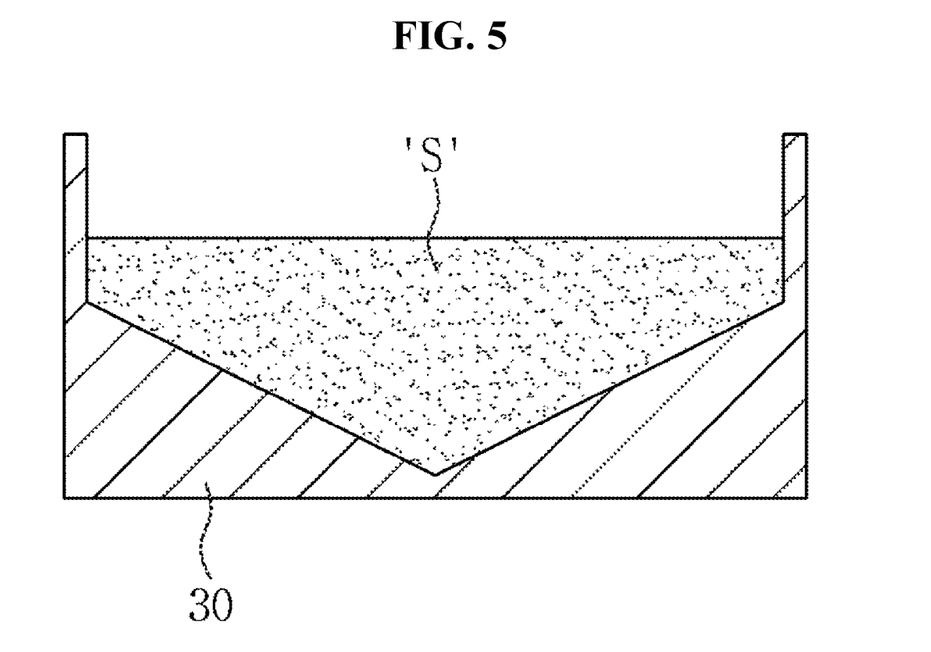
FIG. 5 is a cross-sectional view illustrating a soil storage part of a testing apparatus according to another embodiment of the present invention.

Meanwhile, when the ground test is performed, depths of soil required according to types of tests may vary. However, when the amount of soil increases, a great deal of time is required to achieve a vacuum, and thus it is necessary to minimize the amount of soil according to the tests. To minimize use of soil and meet requirement conditions of the tests, the shapes of bottoms of containers in which soil is contained may vary. For example, to perform a test of a drill that drills soil, deep soil is required. To minimize use of soil and perform a test to a sufficient depth, as shown in FIG. 4, a dent part 31 that is formed concavely downward is formed on a bottom surface of the soil storage part 30, or as shown in FIG. 5, a bottom surface of the soil storage part 30 may be formed concavely downward. In this case, the bottom surface of the soil storage part 30 may have a cone form or a dome form of which a cross-sectional area decreases in a downward direction.

The vacuum generation unit forcibly suctions air in the buffer chamber 10 and the testing chamber 20 to make the insides of the buffer chamber 10 and the testing chamber 20 be in a vacuum state. The vacuum generation unit may have a structure which is the same as or similar to a vacuum generation unit formed in a known thermal vacuum chamber. For example, as shown in FIG. 3, the vacuum generation unit may include suction pipes 62 individually connected to the buffer chamber 10 and the testing chamber 20, vacuum pumps 61 that suction air through each of the suction pipes 62, and the like.

A method of performing a test using the testing apparatus having the above-described structure will be described in detail.

First, a second door 25 of a testing chamber 20 is opened, and a soil storage part 30 in which soil S is stored is inserted into the testing chamber 20 and is positioned at a right position. In this case, the soil S is heated through a pre-conditioning process before being stored in the testing chamber 20, and water and air included in the soil S are removed. When the soil storage part 30 is inserted into the testing chamber 20, the second door 25 is closed, and an opening 22 is closed.

Figure 6A:
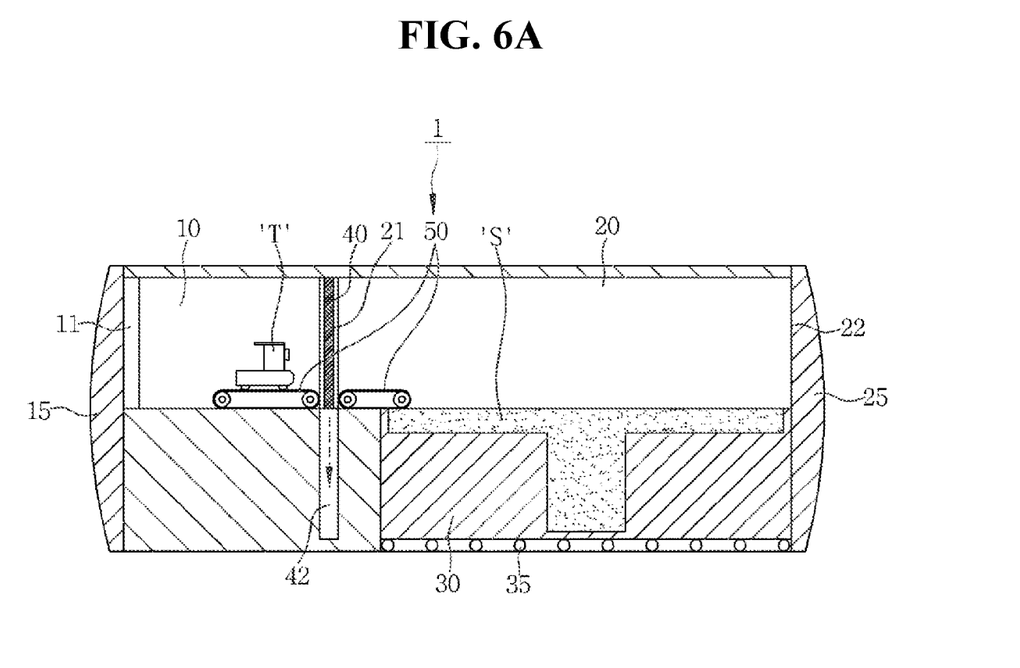
FIGS. 6A to 6D are views sequentially illustrating processes of performing a ground test using the testing apparatus shown in FIG. 1.

Next, the door 15 of the buffer chamber 10 is opened, an object T to be inspected (for example, a construction drill) is inserted into the buffer chamber 10 through an entrance 11, the door 15 is closed, and the entrance 11 of the buffer chamber 10 is sealed (see FIG. 6A).

In this case, a connection passage 21 between the testing chamber 20 and the buffer chamber 10 is closed by a shutter plate 40 so as to separate the testing chamber 20 from the buffer chamber 10.

As described above, when the object T to be inspected is inserted into the buffer chamber 10, the vacuum generation unit operates so as to make the insides of the buffer chamber 10 and the testing chamber 20 be in a vacuum state.

Figure 6B:
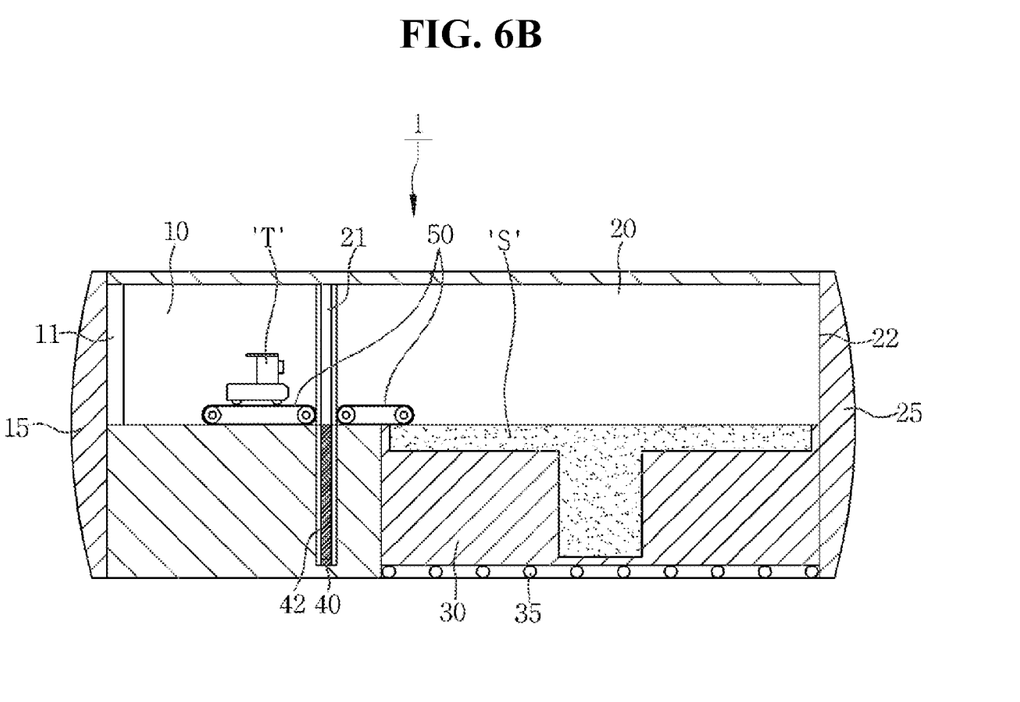

When the insides of the buffer chamber 10 and the testing chamber 20 are made in the vacuum state by the vacuum generation unit, the shutter unit operates in a forward direction such that the shutter plate 40 slides downward so as to be inserted into the shutter accommodation groove 42, and the connection passage 21 is opened. As shown in FIG. 6B, the transfer conveyor 50 operates to transfer the object T to be inspected from the buffer chamber 10 to the testing chamber 20.

Figure 6C:
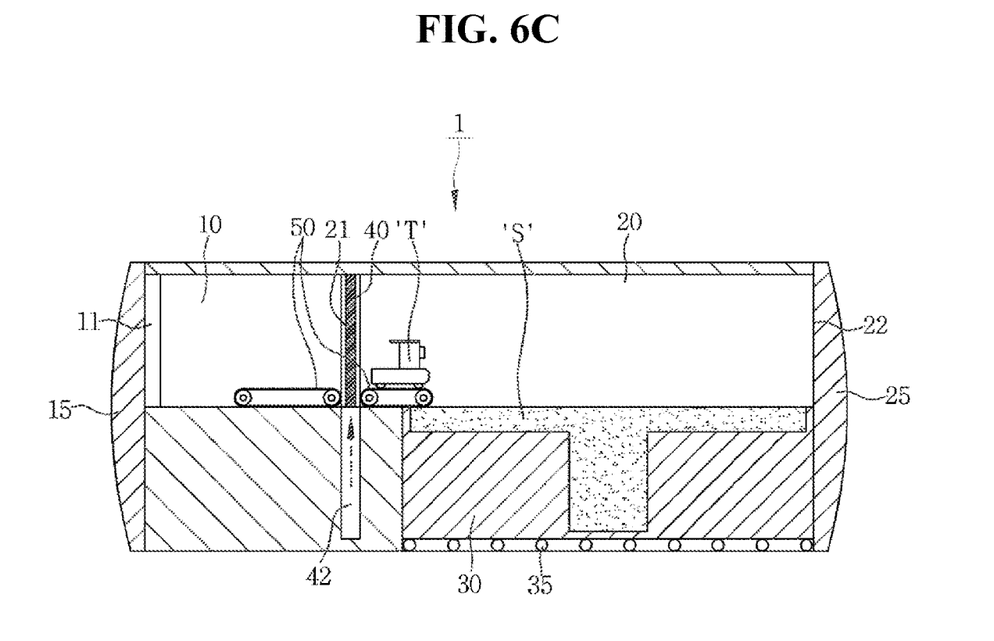

When the object T to be inspected is moved to the inside of the testing chamber 20, as shown in FIG. 6C, the shutter unit operates in a reverse direction such that the shutter plate 40 moves upward so as to close the connection passage 21.

When the object T to be inspected is inserted into the testing chamber 20 and the testing chamber 20 is in the vacuum state, a test robot (not shown) transfers the object T to be inspected on the transfer conveyor 50 to a predetermined position of the soil S on the soil storage part 30, and a predetermined test is performed.

Figure 6D:
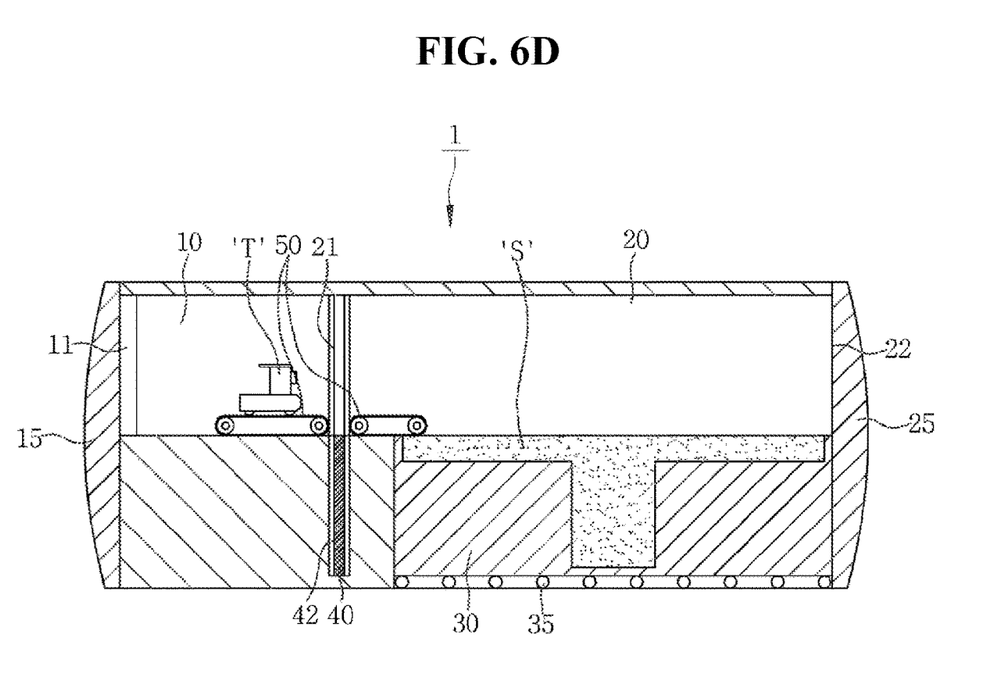

When the ground test of the object T to be inspected on the soil S is completed, the shutter unit operates in a forward direction such that the shutter plate 40 moves downward, the connection passage 21 is opened, and as shown in FIG. 6D, the object T to be inspected is transferred from the testing chamber 20 to the buffer chamber 10.

When the shutter unit re-operates in a reverse direction, the shutter plate 40 moves upward so that the connection passage 21 is closed, and the testing chamber 20 is in a state of being separated from the buffer chamber 10.

In this state, the object T to be inspected is extracted from the inside of the buffer chamber 10 to the outside through the entrance 11 by opening the door 15 of the buffer chamber 10, or the object T to be inspected is treated for the next test and then the first door 15 is closed to isolate the buffer chamber 10 from the outside. When the first door 15 is opened so that the entrance 11 is opened, since external air is introduced into the buffer chamber 10 so that the vacuum state is broken, the first door 15 is re-closed, and a vacuum generation unit operates to remake the buffer chamber 10 be in a vacuum state.

As described above, according to the present invention, the object T to be inspected is inserted into the buffer chamber 10 separated from the testing chamber 20, and the tested object T to be inspected is extracted from the buffer chamber 10, and thus a vacuum state of the testing chamber 20 is continuously maintained without breaking the vacuum state in a process of inserting and extracting the object T to be inspected or a process of replacing measurement equipment. Therefore, it is not necessary to reperform pre-conditioning of the soil S stored in the soil storage part 30 in the testing chamber 20 and a test time is reduced, and thus test efficiency can be substantially increased.

When it is not necessary to perform the ground test using soil S, measurement equipment is inserted into the buffer chamber 10 to perform a predetermined test, and thus various types of tests can be performed according to types and required performance of the object to be tested.

Meanwhile, as described above, one testing apparatus 1 may include the buffer chamber 10, the testing chamber 20, the soil storage part 30, the shutter unit, the vacuum generation unit, and the like, but the testing chamber 20, the soil storage part 30, the shutter unit, the vacuum generation unit, and the like may be formed as one module so that the testing chamber 20 is connected to a conventional thermal vacuum chamber to perform a ground test, and the module may be detachably coupled to the buffer chamber 10.

Further, in the above-described embodiment, when the shutter plate 40 slides downward to be inserted into the shutter accommodation groove 42 and the connection passage 21 is opened so that the object T to be inspected moves to the buffer chamber 10 or the testing chamber 20 through the connection passage 21, a sealing material (not shown) of an edge of the shutter plate 40 accommodated in the shutter accommodation groove 42 may be contaminated. In this case, when the shutter plate 40 closes the connection passage 21, a sealed state is not maintained, and thus a test may not be performed.

Figure 7:
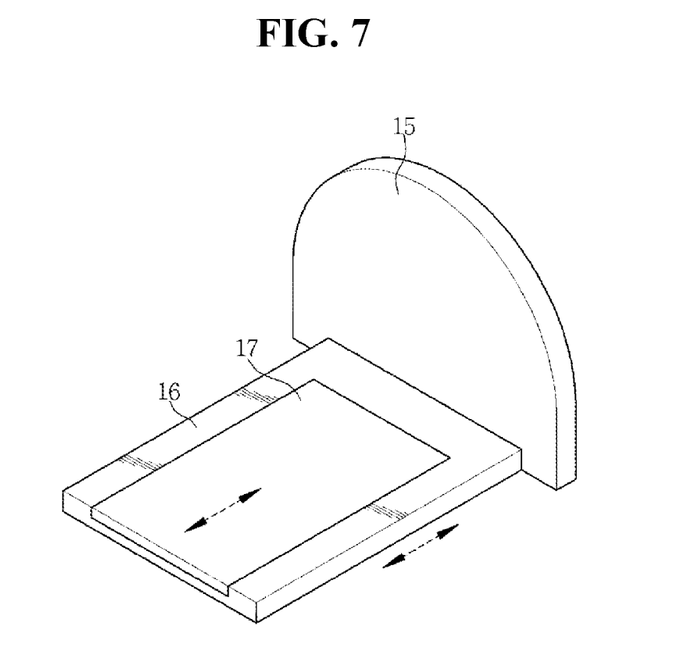
FIG. 7 is a perspective view illustrating main parts of the testing apparatus according to another embodiment of the present invention.
Figure 8:
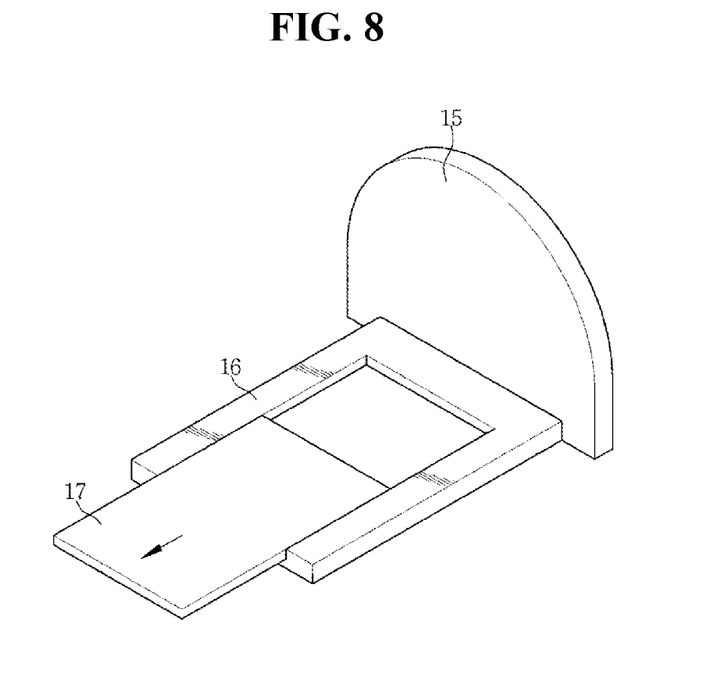
FIG. 8 is a perspective view illustrating an operational example of the main parts of the testing apparatus shown in FIG. 7.
Figure 9:
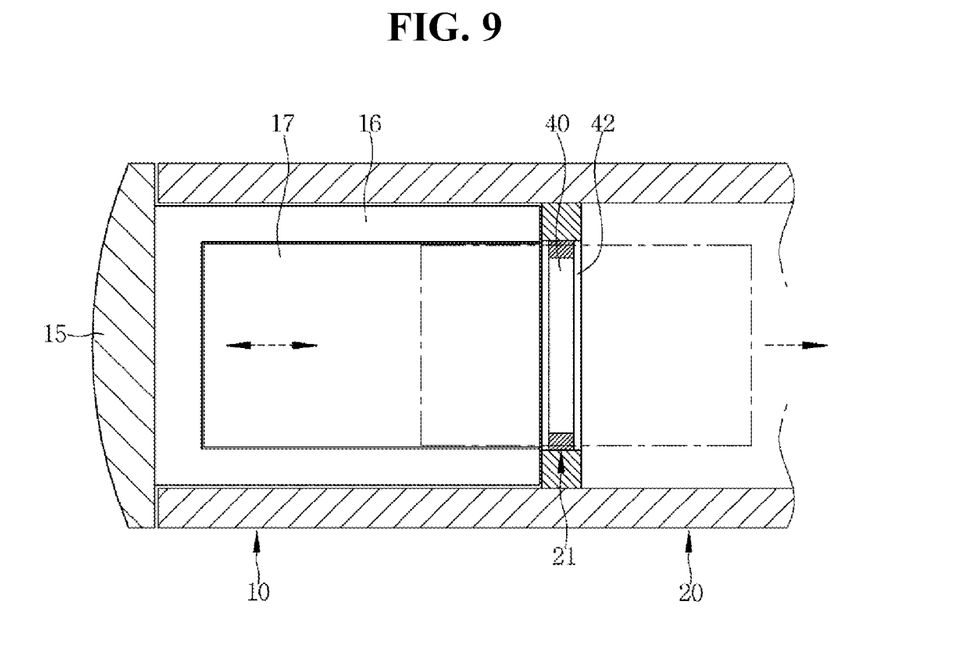
FIG. 9 is a transverse-cross-sectional view of the main parts of the testing apparatus shown in FIG. 7.

To prevent such a case, as shown in FIGS. 7 to 9, a sealing plate 17, on which the object T to be inspected is positioned, is mounted in the buffer chamber 10 of the testing apparatus 1 to be slidable along a lower surface of the connection passage 21, and the sealing plate 17 closes an upper end portion of the shutter accommodation groove 42 in an airtight manner while sliding from the buffer chamber 10 to the testing chamber 20 along the lower surface of the connection passage 21 so as to prevent the sealing material of the edge of the shutter plate 40 from being contaminated when transferring the object T to be inspected from the buffer chamber 10 to the testing chamber 20 or from the testing chamber 20 to the buffer chamber 10.

In the testing apparatus 1 in the embodiment, the sealing plate 17 is fixed to a lower end portion of the first door 15, which opens or closes the entrance 11 of the buffer chamber 10, and is mounted to be slidable to be parallel to an operational plate 16 that laterally moves with the first door 15.

The operational plate 16 has a linear motion system that allows the sealing plate 17 to laterally reciprocate from the operational plate 16. The linear motion system may include a power transmission device including a pneumatic cylinder, a linear motor, a ball screw and a motor, and a plurality of pulleys and a belt, a power transmission device including a motor, a rack gear, and a pinion gear, and a known linear motion system including a motor and the like.

A testing apparatus 1 according to second embodiment of the present invention operates as follows.

Figure 10A:
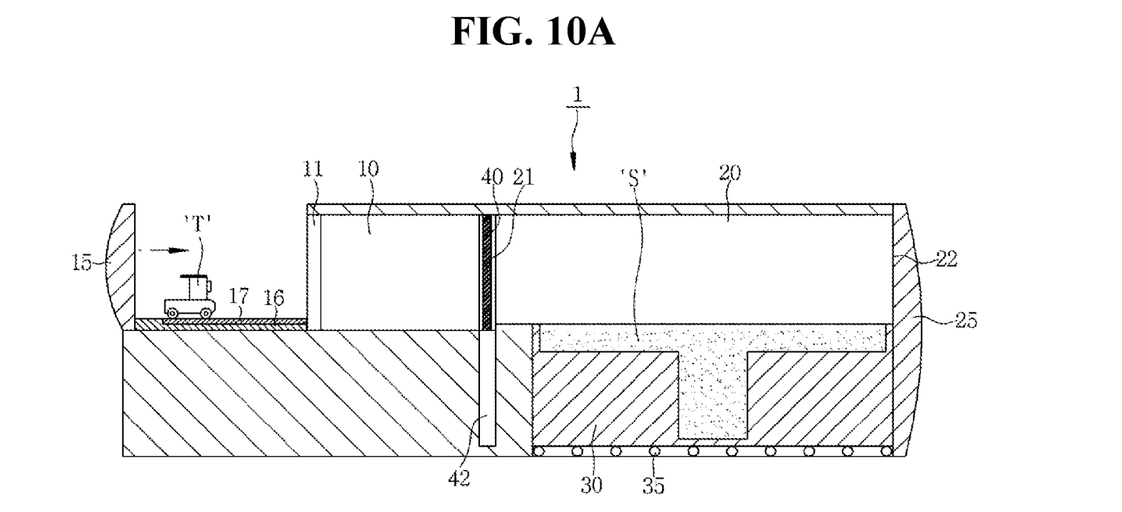
FIGS. 10A to 10C are cross-sectional views illustrating operational examples of the testing apparatus shown in FIG. 7.
Figure 10B:
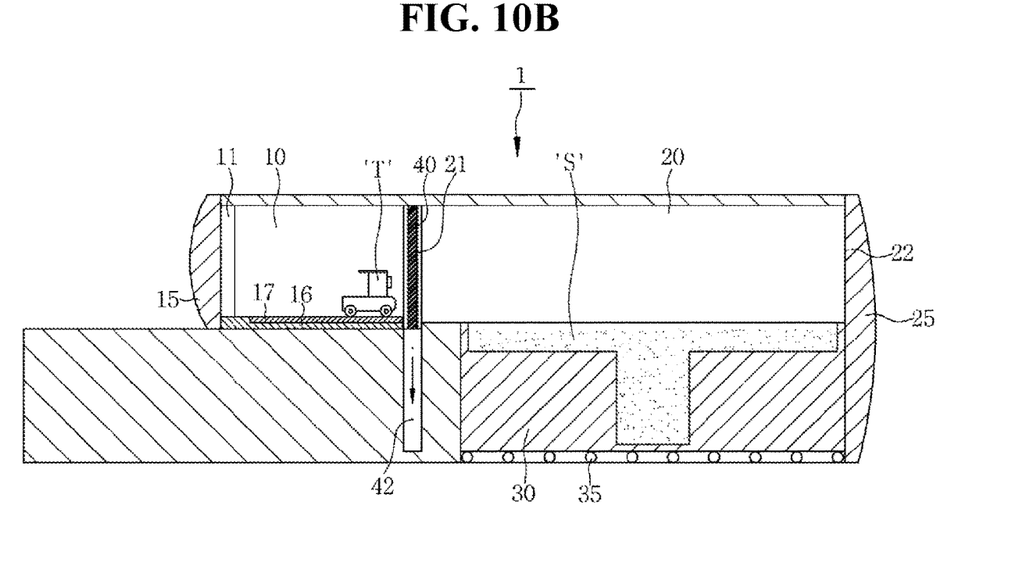

As shown in FIG. 10A, in a state in which the door 15 and the operational plate 16 are extracted to the outside of the buffer chamber 10, the object T to be inspected is positioned on the sealing plate 17 on an upper surface of the operational plate 16, and as shown in FIG. 10B, the door 15 and the operational plate 16 slide to an inside of the buffer chamber 10 so that the object T to be inspected is inserted into the buffer chamber 10, and thus the buffer chamber 10 is sealed.

In this state, the inside of the buffer chamber 10 is made in a vacuum state, the shutter plate 40 is moved downward to an inside of the shutter accommodation groove 42, and the connection passage 21 is opened.

Figure 10C:
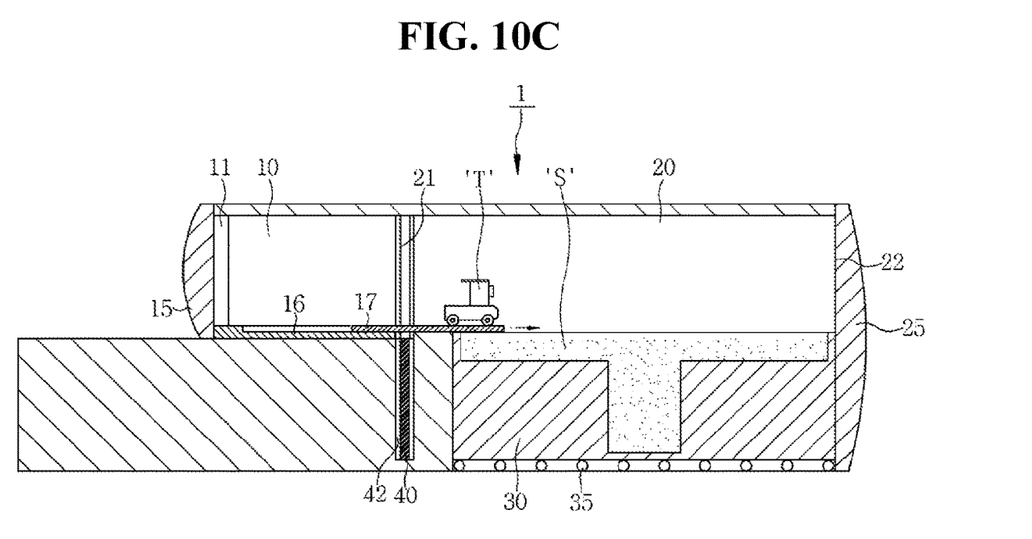

Next, as shown in FIG. 10C, the sealing plate 17 slides to be parallel to the operational plate 16, and the object T to be inspected is transferred to the testing chamber 20. In this case, an upper end portion of the shutter accommodation groove 42 in which the shutter plate 40 is accommodated is sealed in an air tight manner. Therefore, when the object T to be inspected moves into the testing chamber 20, the sealing material of the shutter plate 40 is prevented from coming into contact with foreign materials or out-gas through the upper end portion of the shutter accommodation groove 42, and thus the object T to be inspected can be prevented from being contaminated.

Even when the object T to be inspected that is tested in the testing chamber 20 is transferred to the buffer chamber 10, the shutter plate 40 slides along a lower side of the open connection passage 21 to close the upper end portion of the shutter accommodation groove 42, and thus contamination of the shutter plate 40 can be prevented.

The embodiments of the present invention have been described in detail above, but it should be understood by those skilled in the art that various replacements, additions, and modifications can be made therein without departing from the scope of the present invention defined by the appended claims. Modified embodiments are also included in the scope of the invention defined by the appended claims.

The present invention can be used in apparatus industries that can perform a vacuum ground test of construction equipment and the like by making a vacuum or an extreme environment such as a space environment.

The invention claimed is:

1. A testing apparatus including a vacuum chamber for a ground test, the apparatus comprising:
   a buffer chamber that includes an entrance through which an object to be inspected is inserted and a first door that opens or closes the entrance;
   a testing chamber that is separated from one side of the buffer chamber and includes a connection passage communicating with the buffer chamber;
   a shutter unit configured to open or close the connection passage;
   a soil storage part which is disposed in the testing chamber and in which soil is accommodated for testing the object to be inspected on the ground; and
   a vacuum generation unit configured to suction air in the buffer chamber and the testing chamber so as to make the buffer chamber and the testing chamber be in a vacuum state.

2. The apparatus of claim 1, further comprising a transfer unit configured to transfer the object to be inspected to the buffer chamber or the testing chamber while moving between the buffer chamber and the testing chamber through the connection passage.

3. The apparatus of claim 1, wherein an opening communicating with the outside is formed at one side of the testing chamber, and a second door that opens or closes the opening is mounted on one side of the opening.

4. The apparatus of claim 3, wherein the soil storage part is mounted to be extracted or inserted through the opening when the second door is opened.

5. The apparatus of claim 4, wherein a slide rail that guides the soil storage part inward or outward of the opening is mounted under the testing chamber.

6. The apparatus of claim 1, wherein a bottom surface of the soil storage part is formed concavely downward.

7. The apparatus of claim 1, wherein a dented part that is formed concavely downward is formed on a bottom surface of the soil storage part.

8. The apparatus of claim 1, wherein the shutter unit includes a shutter plate that opens or closes the connection passage while vertically sliding in the connection passage and a shutter operating part that vertically moves the shutter plate.

9. The apparatus of claim 8, wherein a shutter accommodation groove into which the shutter plate is inserted is formed under the connection passage.

10. The apparatus of claim 9, further comprising a sealing plate which is mounted on a lower surface of the buffer chamber to laterally slide along a lower surface of the connection passage and closes an upper end portion of the shutter accommodation groove while transferring the object to be inspected from the buffer chamber to the testing chamber or from the testing chamber to the buffer chamber.

11. The apparatus of claim 10, further comprising an operational plate fixed to a lower end portion of the first door and configured to laterally move with the first door,
wherein the sealing plate is mounted to slide to be parallel to the operational plate.

12. The apparatus of claim 1, wherein the testing chamber, the soil storage part, the shutter unit, and the vacuum generation unit are formed as one module that is detachably coupled to the buffer chamber.

13. A testing method, which is a method of testing an object to be inspected using the testing apparatus according to claim 1, the method comprising:
(S1) inserting a soil storage part in which soil is accommodated into a testing chamber;
(S2) opening a first door of a buffer chamber, inserting an object to be inspected into the buffer chamber through an entrance, and closing the first door;
(S3) making insides of the buffer chamber and the testing chamber be in a vacuum state using a vacuum generation unit;
(S4) operating a shutter unit in a forward direction to open a connection passage and transferring the object to be inspected from the buffer chamber to the testing chamber;
(S5) operating the shutter unit in a reverse direction to close the connection passage;
(S6) performing a predetermined test on the object to be inspected on the soil in the testing chamber;
(S7) operating the shutter unit in the forward direction to open the connection passage and transferring the object to be inspected from the testing chamber to the buffer chamber;
(S8) operating the shutter unit in the reverse direction to close the connection passage; and
(S9) opening the first door of the buffer chamber so that the object to be inspected is extracted from the inside of the buffer chamber to an outside thereof through the entrance.

14. The method of claim 13, further comprising:
before performing the step (S1), performing a pre-conditioning operation that removes water and air included in the soil by heating the soil.

15. The method of claim 13, wherein, when the operation (S3) is performed, the shutter unit closes the connection passage to separate the buffer chamber from the testing chamber, and the buffer chamber and the testing chamber are made in a vacuum state.

* * * * *